US007056520B2

(12) United States Patent
Fitton et al.

(10) Patent No.: US 7,056,520 B2
(45) Date of Patent: Jun. 6, 2006

(54) METHOD AND COMPOSITION FOR THE TREATMENT OF A VIRAL INFECTION

(75) Inventors: J Helen Fitton, Bellevue (AU); Charles Dragar, Berwick (AU)

(73) Assignee: Marinova Party Limited (AU)

( * ) Notice: Subject to any disclaimer, the term of this patent is extended or adjusted under 35 U.S.C. 154(b) by 6 days.

(21) Appl. No.: 10/611,370

(22) Filed: Jun. 30, 2003

(65) Prior Publication Data

US 2004/0087545 A1     May 6, 2004

(51) Int. Cl.
  *A61K 35/78*  (2006.01)
(52) U.S. Cl. .................................. 424/195.17; 424/725
(58) Field of Classification Search ........... 424/195.17, 424/725
  See application file for complete search history.

(56) References Cited

U.S. PATENT DOCUMENTS 5,089,481 A * 2/1992 Muto et al. .................... 514/54

FOREIGN PATENT DOCUMENTS

JP         2002-20403      *   1/2002

OTHER PUBLICATIONS

Fujikawa et al., "Sulphated Polysaccharide of the Thallus of Brown Seaweed Undaria Pinnatifida, Wakame," Nouka, vol. 49, Issue 12, pp. 667-669, 1975.*
Barton, Simon E., et al., The Clinical Management of Recurrent Genital Herpes; Current Issues and Future Prospects, Herpes: 9(1), 15-20 (2002).
Black, W.A.P. et al., Manufacture of Algal Chemicals, J Sci Food Agric, 122-129 (1952).
De Clercq, Erik, et al., Antiviral Drugs: Current State of the Art, J Clinical Virology, 22, 73-89 (2001).
Hoshino, Tomomi, et al., An Antivirally Active Sulfated Polysaccharide from Saragassum Horneri, Biol Pharm Bull, 21, 730-734 (1998).
Hudson, J. B., et al., Aniviral Compounds in Extracts of Korean Seaweeds: Evidence for Multiple Activities, J. Appl. Phycology, 10, 427-434 (1999).
Huleihel, Mahmoud, et al., Antiviral Effect of Red Microalgal Polysaccharides on Herpes Simplex and Varicella Zoster Viruses, J. Appl. Phyco., 13, 127-134 (2001).
Itoh, Hiroko, et al., Antitumor Activity and Immunological Properties of Marine Algal Polysaccharides, Especially Fucoidan, Prepared From Sargassum Thunbergii of Phaeophyceae, Anticancer Res, 13(6), 2045-52 (1993).
Koo, Jae-Guen, et al., Isolation and Purification of Fuciodans from Laminaria Religiosa and Undaria Pinnatifida in Korea, J. Korean Fish Soc., 28(2), 227-236 (1995).
Liu, Ting, et al., Gamma Interferon Can Prevent Herpes Simplex Virus Type 1 Reactivation from Latency in Sensory Neurons, J. Virol., Nov., 75(22), 11178-11184 (2001).

Maruyama, Hiroko, et al., Antitumor Activity and Immune Response of Mekabu Fuciodan Extracted from Sporophyll of Undaria Pinnatifida, In Vivo, 17(3), 245-249 (2003).
Mori, H., et al., Sugar Constituents of Some Sulphated Polysaccharides From the Sporophyllis of Wakame (Undaria Pinnatfida) and Their Biological Activities, Marine Algae in Pharmaceutical Science, vol. 2, 109-121 (1982).
Naesens, Lieve, et al., Recent Developments in Herpesvirus Therapy, Herpes, 8(1), 12-16 (2001).
Nahmias, Andre. J, et al., Sero-epidemiological and -sociological Patters of Herpes Simplex Virus Infection in the World, Scand. J. Infect. Dis Support, 69, 19-36 (1990).
Okinaga, Shigeaki, Shedding of Herpes Simplex Virus Type 1 into Tears and Saliva in Healthy Japanese Adults, Kurume Med J, 47(4), 273-277 (2000).
Ponce, Nora M.A., et al., Fucoidans From the Brown Seaweed Adenocystis Utricularis: Extraction Methods, Antiviral Activity and Structural Studies, Carbohydr Res, 338(2), 153-165 (2003).
Preeprame, Srisomporn, et al., A Novel Antivirally Active Fucan Sulfate Derived From an Edible Brown Alga, Sargassum Horneri, Chem. Pharm. Bull., 49(4), 484-485 (2001).
Schaeffer, David J., et al., Anti-HIV Activity of Extracts and Compounds from Algae and Cyanobacteria, Ecotoxicoligy and Environmental Safety, 45, 208-227 (2000).
Shan, B.E., et al., Immunomodulating Activity of Seaweed Extract on Human Lymphocytes in Vitro, Int J Immunopharmacol, 21(1), 59-70 (1999).
Thompson, K.D., et al., Antiviral Acitivity of Tasmanian Seaweed Extracts Against Clinical Strains of Herpes Simplex Virus (HSV), Abstract, 18th Annual Clinical Virology Symposium, Apr. 28-May 1, Florida 2002.
Thompson, K.D., et al., The Mode of Action of Two Tasmanian Seaweed Extracts Against Herpes Simplex Virus (HSV), Abstract, 27th International Herpes Virus Workshop Conference, Jul. 20-26, Caims, 2002.
Vollstedt, Sabine, et al., Interleukin-12- and Gamma Interferon-Dependant Innate Immunity Are Essential and Sufficient for Long-Term Survival of Passively Immunized Mice Infected with Herpes Simplex Virus Type 1, J Virol, 75(20):9596-600 (2001).
Witvrouw, M., et al., Sulfated Polysaccharides Extracted From Sea Algae as Potential Antiviral Drugs, Gen Pharmacol, 29; 497-511 (1997).
Zeitlin, Larry, et al., Microbicides for Preventing Transmission of Genital Herpes, Herpes, 9(1): 4-9 (2002).
Zhu, Wen, et al., Isolation and Characterization of a Sulfated Polusaccharide From the Brown alga Sargassum Patens and Determination of its Anti-Herpes Activity, Biochem Cell Biol., 81(1), 25-33 (Feb. 2003).

* cited by examiner

Primary Examiner—Susan Coe
Assistant Examiner—S. B. McCormick-Ewoldt
(74) Attorney, Agent, or Firm—Graybeal Jackson Haley LLP

(57) ABSTRACT

Methods and compositions for the treatment, control or prophylaxis of a viral infection in a mammal, the method including administering to the mammal an effective amount of galactofucan sulfate from *Undaria*.

3 Claims, No Drawings

METHOD AND COMPOSITION FOR THE TREATMENT OF A VIRAL INFECTION

FIELD OF THE INVENTION

The present invention relates to a method for the treatment/prophylaxis and control of a viral infection in a mammal. The invention also relates to compositions comprising galactofucan sulfate from the marine algae *Undaria*. This invention has particular application for use in the treatment and prophylaxis of Herpes infections and for illustrative purposes reference will be made to such application.

BACKGROUND OF THE INVENTION

Viruses having a lipid envelope or coat are important human and animal pathogens, Examples of conditions associated with such viruses include HIV, Hepatitis, Ross River and Herpes. The Herpes viruses cause both primary and secondary infections that range from trivial mucosal ulcers to life threatening disorders in immuno-compromised patients. The Herpes group includes HSV-1, HSV-2, Herpes Zoster (chicken pox/shingles), HCMV (human cytomegalovirus), Epstein Barr Virus (EBV), Herpes 6, 7 (Roseola, post transplant infections) and Herpes 8 (associated with Kaposi sarcoma).

Persons infected with a Herpes type virus are typically subjected to cycles of outbreaks where symptoms are experienced and asymptomatic latent periods. During the latent periods, the virus resides in the ganglia where it is inactive and the patient is asymptomatic. However, although asymptomatic, a patient may still be able to infect others. This is known as viral shedding. Reoccurrence of symptoms can occur when the virus is reactivated. Reactivation can be triggered by many different events and is particularly problematic in immunocompromised patients.

The conventional treatment of these infections is with drugs such as acyclovir (ACV) that target the viral DNA polymerase.

There are two generally recognized types of Herpes drug therapy. The first is often referred to as "Outbreak therapy" in which a patient begins drug therapy at the first indication of an outbreak. Following cessation of symptoms, drug therapy is discontinued. A disadvantage of such therapy is that recurrences of infection are not controlled. An alternative therapy is known as "Suppressive therapy" which involves long term doses of maintenance anti-Herpes drug levels. However, whilst the currently available drugs are undoubtedly efficient, they may possibly have side effects, and long-term use has led to the development of resistant viral strains. Such strains now comprise 5% of all HSV infections in immunocompromised patients. There is also patient concern with ongoing drug intake, together with the associated high cost of these drugs.

Subsequently, finding non-toxic alternatives and/or adjuncts to these drugs is extremely important for treatment of patients and also potentially as a prophylactic.

There are a plethora of classes of chemical compounds with putative antiviral effects. One such class is known broadly as the sulfated polysaccharides. The sulfated polysaccharides are an extremely large class of compounds and include sulfated homopolysaccharides, sulfated homooligosaccharides, sulfated heteropolysaccharides, sulfated heteroologosaccharides, sulfoglycolipds, carrageenans and fucoidans. Fucoidans are long branched chains of sugars found in marine algae and echinoderms which include a substantial amount of fucose.

Although encompassed by a single term, the chemical and physical properties of the respective fucoidans vary considerably between species. Such properties include degree of sulfation, molecular weight, degree of branching, linkage positions and fucose content, For example fucoidan from *Fucus vesiculosis* contains about 90% fucose, while fucoidan from *Undaria* contains about 50% fucose and about 50% galactose and is known as galactofucan or fucogalactan sulfate. The fucoldans from echinoderms are substantially linear whereas those from alga are highly branched.

Characterization of the fucoids has been severely inhibited by their complexity and the random nature and heterogeneity of the sugar backbone.

Sulfated polysaccharides are believed to be of potential therapeutic importance because they can mimic sugar rich molecules known as glycosaminoglyeans (GAGs). Examples of GAGs which are important in mammalian physiology are heparin sulfate, dermatan sulfate and chondroitin sulfate. Heparin, for example, is a critical regulatory factor of the blood clotting cascade.

Heparin sulfate receptors on cell surfaces are important in many physiological and pathological processes. They are key entry points for viral entry into some cells and are also necessary for leukocyte movement into tissues and for metastasis. It has been postulated that sulfated polysaccharides such as algal fucoidans may compete for binding sites normally occupied by GAGs and thus inhibit these processes.

Many studies have been conducted with a view to investigating the in vitro anti-viral activity of various sulfated polysaccharides. Studies have generally concentrated on synthetic dextran sulfates, pentosan sulfates, clinically used heparins, and seaweed derived carageenans. One review reports that sulfated homopolysaccharides are more potent than sulfated heteropolysaccharides. (Schaffer DJ et al., 2000 *Ecotoxicology and Environmental Safety* 45:208–227, Witvrouw M et al 1997 *Gen Pharmacol* 29:497–511). Another review expresses concern about the viability of sulfated polysaccharides as in vivo anti-viral agents in view of believed low bloavailability (Luscher-Mattli M, 2000 *Antiviral Chemistry and Chemotherapy* 11(4):249–259). One study which investigated the exploitation of cell-surface GAG's by HIV found that cell-surface heparin sulfate facilitates HIV entry into some cell lines but not primary lymphocytes. The authors expressed caution about extrapolating in vitro results obtained from immortalized cell lines. (Ibrahin J, Griffin P, Coombe D R, Rider C C and James W. Virus Res. 1999 Apr;60(2); 159–69).

Despite the recognized need for alternative anti-viral therapies and the interest in sulfated polysaccharides, to date the present inventors are unaware of any clinical studies on the potential anti-viral effects of sulfated polysaccharides.

Advantageously, it has been discovered that an *Undaria* extract containing galactofucan sulfate is useful in the treatment and/or prevention of conditions associated with viral infections.

SUMMARY OF THE INVENTION

According to a first broad form of the present invention, there is provided a method for the treatment, control or prophylaxis of a viral infection in a mammal, the method including administering to the mammal an effective amount of galactofucan sulfate from *Undaria*.

The viral infection may be caused by coated viruses including. Herpes Viruses and HIV. Preferably, the viral infection treated and/or controlled by the method of the invention may be HSV-1, HSV-2, Vadcella Zoster Virus (in the form of chicken pox or shingles), HCMV, EBV, Herpes 6, Herpes 7 and Herpes 8.

The method of the invention may be particularly suitable for the treatment of viral infections in an immunosuppressed individual. The method of the invention may also be used as an adjunct therapy with other anti-viral therapies.

When the viral infection is one in which the virus may be in an active or latent stage, it is understood that the method of the present invention may be used at any one or both stages of the infection.

According to a further broad form of the invention there is provided a composition for the treatment, control or prophylaxis of a viral infection, the composition comprising an effective amount of galactofucan sulfate from *Undaria*.

The galactofucan sulfate found in *Undaria* is a complex heterogenous carbohydrate whose component sugars are primarily galactose and fucose and small amounts of other sugars. The molecular weight may range from about 30 000 to about 1200 000, typically between about 500 000 to about 1 200 000. Characterization of galactofucan sulfate, and other complex naturally occurring sulfated polysaccharides, is difficult due to the highly complex nature of the molecules. To date, the structure of galactofucan sulfate has yet to be elucidated. However, it is believed that small sections of the molecule may be described as random, alternating or block copolymers of galactose and fucose. Linkage between the sugar units may vary but is believed to be predominantly by 1–3 linkages. The sulfur content is typically between about 4.5–6.5% which suggests a sulfate content of about 18% as $SO_3Na$. This indicates that galactofucan sulfate has an average of about one sulfate group for every two sugar residues.

*Undaria*, the source of the galactofucan sulfate, is a member of the Phaeophyceae (brown) class of marine algae. Any member of the *Undaria* family may be used as the source of the galactofucan sulfate and a preferred source is *Undaria Pinnatifida*. *Undaria Pinnatifida* is an edible seaweed also known as Wakame.

The galactofucan sulfate for use in the method and composition of the invention may be sourced from the whole plant or any part of the plant, such as the leaves, stem, spores, or a combination thereof. If the plants are harvested prior to maturation suitably the whole plant is used.

The galactofucan sulfate may be in the form of dried plant material. Alternatively, or in addition to dried plant material the galactofucan sulfate may be provided in the form of a plant extract. The plant material may be dried prior to the extraction process.

The *Undaria* extract may be obtained by any suitable method to extract plant material that enables at least partial separation of galactofucan sulfate from other plant material. For example, an acid/water mixture may be used to extract the *Undaria*. Preferably, the acid is sulphuric acid. Suitably, the acid/water extract is then neutralised, typically with an alkali metal hydroxide, and filtered or dialysed to remove unwanted components. After filtration or dialysis, the extract may be used as a liquid or freeze dried. Typically such an extract includes at least about 60 wt % galactofucan sulfate.

An especially preferred extraction procedure utilizes an acid/water mixture at a pH of between about 0 to about 2, preferably between about 0 to about 1, at temperatures between about 0 and about 30° C., preferably between about 15 and about 25° C. Whilst not wishing to be bound by theory, it is believed that galactofucan sulfate extracted under these conditions has a similar physical and/or chemical profile to the galactofucan sulfate in its natural form i.e. prior to extraction. Conventional extraction procedures such as those used to extract fucoidans from *Fucus vesiculosis* use more aggressive conditions such as lower pH and/or higher temperatures. It is believed that these conditions may cause hydrolysis and degradation of the galactofucan sulfate which provides an extract having a lower average molecular weight than the "natural" galactofucan sulfate.

Typically a galactofucan sulfate extracted by the above method has a weight average molecular weight of greater than about 100 000, typically greater than about 200 000, preferably greater than about 500 000 Daltons. The upper weight average molecular weight limit is typically about 1 000 000 Daltons.

According to a further form of the invention, there is provided a process for obtaining a galactofucan sulfate extract from *Undaria*, the process comprising extracting plant material from *Undaria* in an aqueous solution having a pH of between about 0 and about 2 at a temperature of between about 0 and about 30° C., neutralizing the extracted solution and subjecting the solution to a separations step so as to separate out material having a molecular weight of less than about 10 000 Daltons.

An especially preferred composition comprises dried *Undaria* sporophyll material. Typically the sporophylls contain between about 8 to about 12 wt % galactofucan sulfate. Whilst not wishing to be bound by theory it is believed that dried sporophylls may include one or more phytochemicals which can act synergistically with the galactofucan sulfate or provide some other beneficial effect. It will be appreciated that any such other beneficial effect may not be limited to an anti-viral effect but may include any effect which may be perceived to be beneficial.

An especially preferred composition comprises dried sporophyll material having elevated levels of galactofucan sulfate. Typically an extract as described above is added to the dried sporophyll material. Typically the level of galactofucan sulfate in the sporophyll/extract mixture is between about 10 to about 20 wt %, typically between about 12 to about 15 wt %.

According to a further broad from of the invention there is provided a composition comprising sporophyll material from *Undaria* and an extract comprising galactofucan sulfate.

The effective amount of galactofucan sulfate for use in the method or composition of the invention may be dependent on the dosage protocol, the intended recipient, the virus and whether the virus is in a latent or active stage. Dosage levels of between about 0.05 g to about 5 g per day, suitably between about 0.9 g and 2.5 g, more suitably between about 0.1375 and about 0.55 g of galactofucan sulfate may be a sufficient amount to affect viral infections. It is to be understood that a person skilled in the art would be able to determine sufficient dosage levels of galactofucan sulfate to administer to a person to obtain effective antiviral activity.

Typical dosages for adult humans experiencing symptoms of an active herpes infection may be between about 0.275 to about 0.55 g per day. Dosage levels for an adult human wherein the virus in the latent stage may be between about 0.075 to about 0.1 375 g per day.

The galactofucan sulfate may be administered in any suitable form. Preferably the galactofucan sulfate is administered orally as a liquid or solid. This mixed extract may be used to form tablets, granules, powder, capsules or like. Solid preparations of the extract of the invention may include any adjuvant or adjuvants which are normally used in the preparation of pharmaceuticals, such as binder, inclusion, excipient, lubricant, disintegrator, wetting agent, etc. For example, the case where administration is as a liquid preparation, the preparation may take the form of liquid for internal use, shake mixture, suspension, emulsion, syrup or the like. These liquid preparations may contain other components ordinarily used in pharmaceutical formulations, such as diluents, excipients, additives and preservatives and the like. Such additives are well known to those of ordinary skill in the art. Pharmaceutical preparations may include any adjuvant or adjuvants which are normally used in the preparation of pharmaceuticals, such as one or more binder, inclusion, excipient, lubricant, disintegrator, wetting agent, etc. It is to be understood that the form of administration is not intended to be limited to oral administration.

DETAILED DESCRIPTION OF THE INVENTION

In order that this invention may be more readily understood and put into practical effect, reference will now be made to the accompanying examples which illustrate preferred embodiments of the invention.

EXAMPLE 1

In one embodiment, the extract of the invention may be made by grinding whole dried plants from *Undaria pinnatifida* to a particle size of less than 1 mm. The ground plant material is added to 1% w/v sulphuric acid in a ratio of 1:1 5 w/v in a 316 stainless steel tank. The mixture is stirred for 1 hour and then the solids removed by filtration on a plate and frame filter press. The solids are resuspended in. 1% w/v sulphuric acid in the ratio of 1:10 and the extraction procedure is repeated.

The combined filtrates are neutralised with sodium hydroxide to a pH of 6.0. The neutral solution is then subjected to ultra filtration and dialysis using 30,000 cut off membranes to remove low molecular weight components and to concentrate the product. This extraction process may provide an extract that has a galactofucan sulfate content of 60 to 70%. The extract is then freeze dried and milled to a particle size of less then 0.4 mm.

The Molecular Weight of the extract was determined by High Performance Liquid Chromatography-Multiangle Laser Light Scattering, Samples were run in 0.1 M $NaNO_3$ at 60° C. on TSK G4 and G5000PWXL columns in series, Detectors were Waters 2410 RI and UV, and Wyatt DAWN-EOS MALLS. Processing was with Wyatt ASTRA software.

Samples were prepared by dissolution in water and left for 24 hours at room temperature prior to analysis. This time prior was selected to allow for uniform dissolution of the extract between samples.

EXAMPLE 2

An extract from *Undaria pinnatifida* was prepared in accordance with the extract process described in Example 1. Dried spore bodies from *Undaria pinnatifida* were similarly milled and then mixed with ground extract in a ratio of about 23:2 to form 560 mg capsules containing about 13.25% galactofucan sulfate, The tests described below utilise these capsules and will hereinafter be referred to as *Undaria* extract capsules.

Treatment of Patients with Active Viral Infections

Patients were recruited for the study by health practitioners. Patients gave verbal informed consent to the study. Health practitioners monitored the patients' health. There are no known adverse effects related to the ingestion of *Undaria*. No other antiviral medications were taken at the same time as the *Undaria* extract capsules. The duration of the study was from one month to 24 months. Patient ages were from less than 10 years up to 72 years.

Fifteen patients with active herpetic viral infections were given four 560 mg *Undaria* extract capsules per day for ten days as a 'therapeutic dose'. All patients except subject 14 (primary zoster infection) were suffering repeat outbreaks of known aetiology (See table 1).

All fifteen patients with active herpetic viral infections experienced relief from symptoms. No adverse side effects were noted during the study.

Two patients (subjects 4 and 5) with noncompliant dosage regimes resolved infections in normal time, but noted no spread of lesions (as occurred during previous outbreaks). Reduction in lesion severity and rapid clearance were noted in two patients (subjects 6 and 7), and pain reduction as compared to previous events was noted by two patients (subjects 2 and 14). Two females with genital HSV-2 had persistent lesions which resolved during the course of treatment (subjects 8 and 10).

In two cases of diagnosed EBV, one clear at four and the other by ten days, In the latter patient a chronic sinus condition also cleared (subjects 11 and 12)

Over ten days, faster drying of zoster lesions and increased speed of normal cycle as compared to previous outbreaks was noted by a male patient (subject 14) although no reduction in pain was reported. In an adult male suffering primary zoster (chicken pox) lesions of whole body (subject 15), pain reduction and rapid healing of lesions were noted.

TABLE 1

Patients with active Herpes infections

| Patient | Sex | Age | Virus | Site infection | Resolution of infection? | If on maintenance, Inhibition of breaks? | Comment |
|---|---|---|---|---|---|---|---|
| 1 | M | 50 | HSVI | Orolabial | Yes, no progression to lesion | Yes, inhibition of further outbreaks on maintenance dose >2 years. | Varied dosage, consistent inhibition. |
| 2 | F | 14 | HSV1 | Orolabial | Yes, very severe outbreak resolved within course. | N/a | Patient noted rapid reduction in pain. |

TABLE 1-continued

Patients with active Herpes infections

| Patient | Sex | Age | Virus | Site infection | Resolution of infection? | If on maintenance, Inhibition of breaks? | Comment |
|---|---|---|---|---|---|---|---|
| 3 | F | 72 | HSVI prodrome | Orolabial (prodrome) and ocular conjunctiva | Yes, no progression to lesion | Yes, continued Inhibition of low grade conjunctival HSVI for three months | Notes improvement in skin condition. |
| 4 | M | 40 | HSVI prodrome | Orolabial | Yes, in normal time. | N/a | Not taken consistently. No benefit noted but no spread of lesion. |
| 5 | F | 50 | HSVI active l sion | Orolabial | Yes, in n rmal time | N/a | No spread of lesion and pain reduced. Took half dose only. |
| 6. | F | 47 | HSVI | Orolabial | Yes, reduction in lesion severity | N/a | No recurrence, no spread of lesion. |
| 7. | F | 47 | HSVI | Orolabial | Yes, rapid clearance compared to previous. | N/a | Post chemotherapy outbreak (breast cancer) |
| 8 | F | 20 | HSVII | Genital | Yes, lesions cleared. | N/a | |
| 9 | F | 42 | HSVII | Genital | Yes. Existing lesion healed. | Yes, inhibition of further outbreaks on maintenance dose 3 mths. | Prior two weekly outbreaks of ACV resistant strain of HSVII. |
| 10 | F | 23 | HSVII | Genital | Yes, chronic lesion healed | N/a | |
| 11 | F | 17 | EBV | systemic | Yes | N/a | Normal blood exam after 4 days course. |
| 12 | F | <10 | EBV | Systemic | Yes, EBV symptoms absent at ten days | N/a | Three capsules per day Chronic sinus infection also cleared |
| 13 | F | 85 | Zoster (shingles) | Torso | Yes | Yes, inhibition for two months. | Relief from lesions at 4 capsules per day |
| 14. | M | Adult | Zoster (chicken pox) | Whole body sores | Yes | N/a | Pain reduction, rapid clearing of lesions. |
| 15 | M | 40 | Zoster (shingles) | T7, 8, dermatome Right side | Yes | N/a | Faster drying of lesions, increased speed of cycle, no change in pain |

Treatment of Latent Infections

Six patients with latent HSV-1 or 2 were given two 560 mg capsules of *Undaria* extract per day as a 'maintenance dose'. One patient (3) took four 560 mg capsules per day.

All six patients on maintenance doses noted inhibition of further outbreaks of infection (Table 2). No adverse side effects were noted during the study.

HSV-1 outbreaks were inhibited in two patients taking a maintenance dose over three months and two years respectively (subject 1 and 2). Low grade HSV-1 associated keratoconjunctivitis in the former patient was also inhibited.

*Undaria* extract ingestion correlated with inhibition of a previously persistent HSV-2 infection for three months in subject 4. In this patient, the infection was acyclovir (ACV) resistant and outbreaks had been apparent on a two weekly basis for over a year. ACV is a nucleic acid inhibitor that prevents viral replication after the virus has entered the cell and is commonly used to treat Herpes.

HSV-2 outbreaks at the genital site were inhibited in two other female patients whilst taking a maintenance dose of two capsules per day, for one month (subjects 5 and 6).

Low grade persistent Herpes zoster (shingles) lesions of the whole torso were inhibited for two months in an elderly patient whilst maintaining a dose of four capsules per day (3).

In vitro Effects of *Undaria* Extracts on HSV and Human Cytomegalovirus

An *Undaria* extract capsule was mixed 1:40 w/v with distilled water and boiled for 5 minutes. The liquid was filtered through a 0.45 µM filter for sterilization and stored at −20° C. An aliquot of the preparation was dried and the weight was obtained to determine the concentration. The concentration used was the dry weight of the dissolved solids present.

Immortalized human fibroblasts, HF cells, were grown in Minimal Essential Media supplemented with glutamine, antibiotics, and 10% foetal bovine serum (FBS). Maintenance medium was supplemented with 1% FBS. Laboratory strains of HSV and HCMV were tested in this study. A stock of each virus was grown in cultured HF cells and aliquots were frozen at −70° C. The titre of each virus was determined by a plaque assay using HF cells in 24-well plates with an agarose overlay.

Herpes viruses were assessed for infectivity of human fibroblasts cells in vitro. Inhibition by *Undaria* extract was noted as shown in Table 3.

TABLE 2

Patients with latent Herpes infections.

| Patient | Sex | Age | Virus | Site of infection | Also treated for active infection? | Inhibition of outbreak whilst on maintenance dose? | Comments |
|---|---|---|---|---|---|---|---|
| 1 | M | 50 | HSVI | Orolabial | Yes Existing lesion healed. | Yes, inhibition of further outbreaks on maintenance dose >2 years. | Varied dosage, consistent inhibition. |
| 2 | F | 72 | HSVI prodrome | Orolabial (prodrome) and ocular conjunctiva | Yes, no progression to lesion | Yes, continued Inhibition of low grade conjunctival HSVI for three months | Notes improvement In skin condition. |
| 3 | F | 85 | Zoster (shingles) | Torso | Yes | Yes, inhibition for two months. | Relief from lesions requires 4 capsules per day |
| 4 | F | 42 | HSVII | Genital | Yes, Existing lesion healed. | Yes, inhibition of further outbreaks on maintenance dos 3 m nths. | Prior two weekly outbreaks of ACV resistant strain f HSVII. |
| 5 | F | 41 | HSVII | G nital | No | Yes, inhibition on two capsules per day for 1 month. | Did not take during active lesion outbreak. |
| 6 | F | 36 | HSVII | Genital | No | Yes, inhibition on two capsules per day for 1 month. | Did not take during active lesion outbreak. |

TABLE 3

ICSO for Undaria extract as measured by infectivity of HSV1, HSV2 and HCMV (human cytomegalovirus) in human fibroblasts.

| Herpes virus | Undaria extract Capsule mixed 1:40 w/v with water |
|---|---|
| HSV - 1, strain F | 3.1 ug/ml |
| HSV - 2, strain G | 1.6 ug/ml |
| HCMV, AD169 | 2.5 ug/ml |
| HCMV, D16 | 2.5 ug/ml |

In vitro Effects of Extracts on HSV

Two *Undaria* extracts containing galactofucan sulfate were evaluated to determine their antiviral activity against clinical strains of HSV. Extract No. 1 was obtained by boiling *Undaria* sproprhyll in water for 10 minutes. Extract No. 2 was obtained as per the extraction procedure described in Example 1.

The extracts were significantly more active against clinical strains of HSV-2 than against HSV-1, p<0.001. The mode of action was unknown but preliminary testing indicated the mode of action may be the inhibition of viral entry into the host cell.

HSV-1 strain F and HSV-2 strain G were tested in binding assays and also in post-binding antiviral assay. The viruses were tested in 96-well microtiter plates format using human fibroblast cells. The viruses were inoculated at MOIs of 0.1 and 0.25. For the binding assays, the effective concentration of extract ranged from 128 to 2 µg/ml. For the post-binding assays, the concentrations ranged from 4000 to 31 µg/ml.

The results of the assay tests are shown in Tables 4 and 5.

TABLE 4

Inhibition of binding, µg/ml.
(MOI = Multiplicity of Inf ction)

| Virus | Strain | Undaria Extract No. 1 | Undaria Extract No. 2 |
|---|---|---|---|
| HSV-1, MOI = 0.1 | F | 32 | 16 |
| HSV-1, MOI = 0.25 | F | 128 | 32 |
| HSV-2, MOI = 0.1 | G | 2.0 | 0.125 |
| HSV-2, MOI = 0.25 | G | 4.0 | 0.25 |

TABLE 5

Post-binding inhibition µg/ml.
(MOI = Multiplicity of Infection)

| Virus | Strain | Undaria Extract No. 1 | Undaria Extract No. 2 |
|---|---|---|---|
| HSV-1, MOI = 0.1 | F | >4000 | >4000 |
| HSV-1, MOI = 0.25 | F | >4000 | >4000 |
| HSV-2, MOI = 0.1 | G | >4000 | >4000 |
| HSV-2, MOI = 0.25 | G | >4000 | >4000 |

The extracts inhibited HSV from binding to cellular receptors in this in vitro assay. There was, however, no post-binding inhibition of HSV by the extracts at concentrations up to 4000 µg/ml. These results indicate that the extracts are effective in inhibiting HSV by blocking attachment and entry into the host cells.

T Cell Stimulation in vitro

T cell mitogenicity was evaluated by chromium uptake. Whole T cell preparations were obtained from buffy coats from human blood samples. They were incubated in RPMI supplemented with 10% heat inactivated foetal calf serum, 5 mM L-glutamine, $5 \times 10^{-5}$M 2-mercaptoethanol and 30U/ml gentamycin. Incubation for 72 hours was at 5% $CO_2$, 37° C. in 24 well plates. T cell mitogenicity was assessed by radioactive chromium uptake. Cells were incubated with either *Undaria* extract (at 25, 125 and 250 mcg/ml as 1%, 5% or 10% of total culture volume from a stock solution at 2.5 mg/ml) or with the known mitogens (PHA) (1 mcg/ml) or Concanavalin A (ConA) (1 mg/ml). Each concentration was assessed in triplicate (n=3)

The *Undaria* extract was assessed for effects on whole human T cell preparation in vitro. After incubation with the *Undaria* extract or mitogens PHA and ConA, for 72 hours the relative uptake of chromium was assessed as a measure of mitogenicity. The lowest concentration of *Undaria* extract tested (25 mcg/ml) exerted a four fold mitogenic effect on T cells, over 50% of the mitogenic potency of the known mitogens PHA (six fold) and ConA (seven fold). Paradoxically, increased concentrations of the whole extract showed decreasing effects on mitogenic activity. This may be accounted for by the increasing physical inhibition due to increased viscosity in the culture media, or the increasing concentration of unidentified inhibitory components present in the extract.

Additional studies illustrated little effect on NK cell activity and no effects on L929 fibroblast growth over 24 or 72 hours (results not shown). There was no bacterial contamination of the *Undaria* extract (results not shown), thus the presence of bacterial lipopolysaccharides (which may also act as mitogens) was ruled out.

The studies carried out in Example 2 assessed the effects of *Undaria* extracts containing galactofucan sulfate in patient studies and in vitro. The extracts of the invention was ingested by patients suffering active or latent herpes infections. Results indicated firstly, increased rate of healing, and secondly, inhibition of outbreaks in cases of HSV-1, HSV-2, ACV resistant HSV-2, and zoster. There were no adverse side effects noted, and *Undaria* extracts was well tolerated by all subjects. Reduced pain levels were noted in some cases, which may be a result of the increased rate of healing.

A particularly noteworthy result in this study was inhibition of an ACV resistant case of HSV-2. HSV-2 is a sexually transmitted disease of increasing incidence. In part, this is due to the fact that partner transmission may occur during asymptomatic shedding or unrecognised minor outbreaks. Suppressive therapies such as ACV have been tested for their ability to inhibit shedding. However, for long-term use, non toxic alternatives such as *Undaria* extracts may be preferred by patients, who perceive long term conventional drug use as detrimental. In addition, *Undaria* extracts may reduce the generation of resistant strains which arise through prolonged use of drugs such as ACV.

This study shows that ingestion of *Undaria* extracts of the invention is associated with resolution, reduced pain and outbreak inhibition of Herpes virus infections resulting in increased healing rates inpatients with active infections. In addition, patients with latent infection remained asymptomatic whilst ingesting the *Undaria* extracts containing galactofucan sulfate. The extracts of the invention inhibited Herpes viruses in vitro and was mitogenic to human T cells in vitro.

Although the experimental results are only in respect of Herpes Viruses, it is to be understood that any virus which adheres to the cell through a similar mechanism as Herpes Group Viruses would also be inhibited by *Undaria* extracts of the invention.

In the specification the terms "comprising" and "containing" shall be understood to have a broad meaning similar to the term "including" and will be understood to imply the inclusion of a stated integer or step or group of integers or steps but not the exclusion of any other integer or step or group of integers or steps. This definition also applies to variations on the terms "comprising" and "containing" such as "comprise", "comprises", "contain" and "contains".

It will of course be realised that while the foregoing has been given by way of illustrative example of this invention, all such and other modifications and variations thereto as would be apparent to persons skilled in the art are deemed to fall within the broad scope and ambit of this invention as is herein set forth.

The invention claimed is:

1. A composition for the treatment, control or prophylaxis of a viral infection in a mammal, the composition comprising an effective amount of a galactofucan sulfate obtained from *Undaria*, wherein the galactofucan sulfate has a weight average molecular weight of greater than about 500 000 Daltons.

2. The composition of claim 1 in a form suitable for oral administration.

3. The composition of claim 1 wherein the galactofucan sulfate has a weight average molecular weight of 500 000 to 1 000 000 Daltons.

* * * * *

UNITED STATES PATENT AND TRADEMARK OFFICE
CERTIFICATE OF CORRECTION

| | | |
|---|---|---|
| PATENT NO. | : 7,056,520 B2 | Page 1 of 1 |
| APPLICATION NO. | : 10/611370 | |
| DATED | : June 6, 2006 | |
| INVENTOR(S) | : J. Helen Fitton and Charles Dragar | |

It is certified that error appears in the above-identified patent and that said Letters Patent is hereby corrected as shown below:

On title page item [56] Insert

Certified Copy of Priority Document is being submitted in order to perfect priority claim.

This application claims priority from Australian Application No. 2002952368, which was filed on October 31, 2002.

Signed and Sealed this

Twenty-second Day of May, 2007

JON W. DUDAS
*Director of the United States Patent and Trademark Office*